(12) United States Patent
Bataille

(10) Patent No.: US 12,257,402 B2
(45) Date of Patent: Mar. 25, 2025

(54) MARKER BAND PULL WIRE ASSEMBLY AND METHOD OF USE THEREOF

(71) Applicant: NORTH STAR MEDICAL INC., Montréal (CA)

(72) Inventor: Olivier Bataille, Lachine (CA)

( * ) Notice: Subject to any disclaimer, the term of this patent is extended or adjusted under 35 U.S.C. 154(b) by 801 days.

(21) Appl. No.: 17/494,564

(22) Filed: Oct. 5, 2021

(65) Prior Publication Data
US 2022/0023595 A1    Jan. 27, 2022

Related U.S. Application Data

(63) Continuation of application No. PCT/CA2020/050377, filed on Mar. 23, 2020.

(60) Provisional application No. 62/839,875, filed on Apr. 29, 2019.

(51) Int. Cl.
*A61M 25/01* (2006.01)

(52) U.S. Cl.
CPC .... *A61M 25/0147* (2013.01); *A61M 25/0108* (2013.01); *A61M 25/0136* (2013.01); *A61M 2025/015* (2013.01)

(58) Field of Classification Search
None
See application file for complete search history.

(56) References Cited

U.S. PATENT DOCUMENTS

| | | | |
|---|---|---|---|
| 4,998,916 A * | 3/1991 | Hammerslag | A61M 25/0144 604/95.04 |
| 5,403,297 A | 4/1995 | Imran | |
| 6,475,214 B1 | 11/2002 | Moaddeb | |
| 6,945,956 B2 | 9/2005 | Waldhauser et al. | |
| 9,462,931 B2 | 10/2016 | Greig et al. | |
| 9,808,311 B2 | 11/2017 | Wang et al. | |
| 2003/0181855 A1 | 9/2003 | Simpson et al. | |
| 2011/0270229 A1 | 11/2011 | Tanaka et al. | |
| 2013/0110083 A1 | 5/2013 | Koehler | |
| 2016/0367787 A1 | 12/2016 | Van Hoven et al. | |

(Continued)

FOREIGN PATENT DOCUMENTS

| DE | 202018102207 U1 | 4/2018 |
|---|---|---|
| WO | 2013/069019 A2 | 5/2013 |

(Continued)

OTHER PUBLICATIONS

International application No. PCT/CA2020/050377 International Search Report dated Jul. 3, 2020.

(Continued)

*Primary Examiner* — Manuel A Mendez
(74) *Attorney, Agent, or Firm* — Anglehart et al.

(57) ABSTRACT

A pull wire assembly for integrating into and anchoring an end of a steerable catheter or introducer sheath used in medical procedures; it has a pull ring made at least in part from a radiopaque material that, when integrated into the end of the steerable catheter or the introducer sheath, allows for visualizing the end of the steerable catheter or the introducer sheath during a medical procedure; and one or more pull wires with a different material composition from that of the pull ring, wherein the one or more pull wires are each fused to the pull ring, wherein the fusion results in an amalgam of the radiopaque material and the pull wire material composition.

11 Claims, 11 Drawing Sheets

(56) References Cited

U.S. PATENT DOCUMENTS

| | | |
|---|---|---|
| 2017/0281269 A1 | 10/2017 | Ishikawa et al. |
| 2018/0001058 A1 | 1/2018 | Schlesinger |
| 2018/0264230 A1 | 9/2018 | Funk et al. |
| 2018/0326182 A1 | 11/2018 | Jung, Jr. |
| 2018/0344980 A1* | 12/2018 | Contreras ......... A61M 25/0147 |

FOREIGN PATENT DOCUMENTS

| | | |
|---|---|---|
| WO | 2015/011817 A1 | 1/2015 |
| WO | 2018/022402 A1 | 2/2018 |
| WO | 2018/174712 A1 | 9/2018 |

OTHER PUBLICATIONS

International application No. PCT/CA2020/050377 Search Strategy dated Jul. 3, 2020.

International application No. PCT/CA2020/050377 Written Opinion of the International Searching Authority dated Jul. 3, 2020.

\* cited by examiner ent application is a continuation of international
MARKER BAND PULL WIRE ASSEMBLY AND METHOD OF USE THEREOF The present application is a continuation of international PCT patent application No. PCT/CA2020/050377, filed Mar. 23, 2020, that claims priority from U.S. provisional patent application No. 62/839,875 filed on Apr. 29, 2019, incorporated herein by reference.

TECHNICAL FIELD

The present disclosure relates to medical equipment, and more particularly to steerable catheters and introducers sheaths.

BACKGROUND

Catheters are commonly used to perform medical procedures either directly or indirectly by a medical professional. The medical professional can be located directly at the side of the patient and using a direct catheter or sheath with a handle and shaft and with a mechanical deflection mechanism in which case the deflection mechanism is directly part of the catheter handle. In the case where a medical robot is being used, the deflection mechanism may still be part of the catheter or sheath handle or the pull wire or pull wires in a case of a dual deflection or single deflection with active return catheter may be protruding out of the catheter shaft and no handle is present and the deflection wires can be attached to the robot where it can utilize its own motorized deflection mechanism. In either case the catheter is used in various medical applications such as but not limited to interventional cardiology, electrophysiology, urology and oncology. A catheter or sheath used in such varying applications has a varying length shaft body having a distal end. Steering the distal end of a catheter can be difficult, especially as the elongate body passes through a tortuous vascular path. Such devices are typically used in minimally invasive procedures and require visualization such as x-ray, dynamic x-ray also known as fluoroscopy. In the case of x-ray or fluoroscopy it is important to be able to locate and visualize the tip of the catheter or sheath for various medical and procedural reasons. The design requirements of visualization and deflection are often in conflict as you want the marker band to be as near the distal end or tip of the catheter as possible and you want the deflection mechanism to be as distal as possible. The two are typically made out of metal or alloys that have appropriate properties of their distinct mission. The typical catheter or sheath marker band is placed most distally without compromising the a-traumatic function of the low durometer tip of the sheath or rounded end catheter and is made out of a radio-opaque alloy such as platinum-iridium. The pull wire ring is typically made out of treated stainless steel to have the highest young's modulus possible. During the assembly of the catheter of sheath shaft, it is important not to have the two rings too close to each other as they create a large heat-sink during the polymer reflow process and may prevent the different layers and durometer to reflow and homogeneously together.

Catheter tip steering is often accomplished with the use of one or more pull wires attached to a pull ring within the distal end of the catheter shaft at one end, and coupled to a steering control mechanism housed within the handle at the other end or the pull wire is activated by an external force such as a medical robot. Manipulation of the steering control mechanism will deflect the catheter tip through pulling or releasing pull force pressure on the one or more pull wires.

The pull force exerted on a pull wire within a standard-sized catheter is often quite large, for example, in excess of ten pounds, and the pull force required is increased for thicker or longer catheters. Therefore, the point of connection between a pull wire and the pull ring is able to withstand this force in order to preserve the integrity of the steering system.

A catheter or deflectable sheath shaft is typically constructed out of polymers with varying durometer so that once constrained in a confined space only the tip with the smaller durometer combination will deflect radially towards the pull wire.

The pull wires are typically welded to the pull wire ring and the maximum force and pressure, the articulation point of the assembly is where the wire is welded to the ring. However, this joining method is very susceptible to stress fractures and peeling as a pull force is exerted repeatedly over time (referred to herein as "destructive pull force" to distinguish from the pull force necessary to steer the catheter tip), it is not uncommon for pull rings to become detached from the inside of the catheter shaft and creep away from the distal end of the catheter as a result of repeated deflections and manipulations. It is also not uncommon during V&V testing to see that the breaking point of the wire is where the welding occurred and the breaking pull force is less than an order of magnitude away from the maximum operating pull force. This is especially true for cardiac introducer sheaths either for TAVR or balloon PV ablation where the catheter inside the deflectable sheath sees very high deflection forces.

SUMMARY

Therefore, it would be advantageous to have a pull ring that would also act as a marker band, where the combining of the pull ring and the marker band reduces the number of ring components at the distal end of the sheath or catheter. As such, this reduces rigidity of the end of the catheter and sheath (thus improving navigation by increasing the flexibility of the distal end) and reduces manufacturing cost.

As such, the present disclosure relates to a pull wire assembly with a pull ring to which one or more pull wires are attached that is made from a radiopaque material, allowing for visualizing the pull ring by performing, for instance, fluoroscopy. As such, the pull ring also acts as a marker band. Exemplary materials used to make the pull ring may be, for instance, tantalum, molybdenum, a tantalum alloy, a molybdenum alloy or a combination thereof.

By providing a pull ring also acting as a marker band, the manufacturing process of tubular medical devices such as steerable catheters and introducer sheaths is simplified while maintaining a tensile strength that is comparable to the steerable catheters and introducer sheaths as are known in the art.

Alternatively, the pull ring may include one or more apertures located on the pull ring to prevent delamination of the pull ring from the shaft of the steerable catheter or medical device. The pull ring may also include a receiving slot that may have a "U" shape notch to receive a flattened end of a pull wire.

Moreover, it would be advantageous to have a pull ring where the hinging point of the deflection mechanism is away from the weld. As such, this would reduce the risk of detachment of the pull ring from the inside of the shaft of the sheath or catheter, or stress fractures of the ring.

The present disclosure also relates to a pull ring including apertures that are positioned radially asymmetrically on the pull ring and are closer to a proximal end of the pull ring than to a distal end of the pull ring. This asymmetric distribution of the apertures allows for bending and stress of the pull ring under the force exerted by the pull wires at points that are distinct from the points where the pull wires are joined to the pull ring, thus reducing the risk of fracturing the pull ring or detaching the pull wires from the pull ring.

The present disclosure also relates to a marker band that is composed from a radiopaque material and coated with gold for improving visualization of the distal end of the medical device during a medical procedure.

A broad aspect of the present disclosure is a pull wire assembly for integrating into and anchoring an end of a steerable catheter or introducer sheath used in medical procedures. The pull wire assembly includes a pull ring made at least in part from a radiopaque material that, when integrated into the end of the steerable catheter or the introducer sheath, allows for visualizing the end of the steerable catheter or the introducer sheath during a medical procedure. The pull wire assembly includes one or more pull wires with a different material composition from that of the pull ring, wherein the one or more pull wires are each fused to the pull ring, wherein the fusion results in an amalgam of the radiopaque material and the pull wire material composition.

In some embodiments, the fusion may result in a homogenous amalgam of the radiopaque material and the pull wire material composition.

In some embodiments, the pull ring may be made from tantalum, molybdenum, a tantalum alloy, a molybdenum alloy or a combination thereof.

In some embodiments, the pull ring may be gold-plated.

In some embodiments, the pull ring further may include a diving board extending from the pull ring for each of the one or more pull wires, and wherein the each of the one or more pull wires may be respectively fused to each diving board.

In some embodiments, side portions of the each diving board may be of an arcuate shape with a radius that blends into the pull ring for deflecting force exerted by the one or more pull wires onto the pull ring.

In some embodiments, the each diving board may include a notch for receiving the pull wire that is fused to the diving board.

In some embodiments, the notch may be of a depth that is less than a thickness of the diving board.

In some embodiments, the pull ring may include apertures interspersed about the pull ring.

In some embodiments, the pull ring may include a proximal end and a distal end defining a width of the pull ring, wherein the one or more pull wires may each be fused to the pull ring at a respective location that is closer to the proximal end of the pull ring than the distal end of the pull ring.

In some embodiments, there may be at least one of the apertures that is located closer to the proximal end of the pull ring than the distal end of the pull ring, and wherein the apertures may be radially distributed at nonuniform intervals with respect to one-another.

In some embodiments, at least some of the apertures may have a three-lobe cross-sectional shape.

In some embodiments, the one or more pull wires may be made from steel.

In some embodiments, the one or more pull wires may be made from a nickel titanium alloy.

In some embodiments, for each of the one or more pull wires, an end that is fused to the pull ring may be flattened.

Another broad aspect is an introducer sheath for use in medical procedures including the pull wire assembly as defined herein, wherein the pull wire assembly is integrated into the introducer sheath and the pull ring is anchored to at an end of the introducer sheath.

Another broad aspect is a steerable catheter device for use in medical procedures. The catheter devices includes an elongated body with a proximal end and a distal end, the elongated body comprising an inner lumen; and the pull wire assembly as defined herein wherein the pull ring is integrated into the elongated body at the distal end of the elongated body, wherein the one or more pull wires runs along the elongated body from the distal end of the elongated body to the proximal end of the elongated body, and wherein a position of the distal end of the elongated body may be viewed during a medical procedure by visualizing the position of the pull ring.

In some embodiments, the catheter device may include a handle located at the proximal end of the elongated body.

In some embodiments, the handle may include a steering control mechanism, and wherein tension applied to the one or more pull wires by the steering control mechanism causes the elongated body to deflect.

Another broad aspect is a use of the introducer sheath as defined herein or of the catheter device as defined herein for visualizing the tip of the introducer sheath or of the catheter device during a medical procedure.

In some embodiments, the medical procedure may be a cardiac procedure.

Another broad aspect is a method of steering the catheter device as defined herein in a patient during a medical procedure. The method includes applying tension to at least one of the one or more pull-wires fused to the pull ring, resulting in a force being applied to the pull ring that is integrated into the distal end of the elongated body, causing the elongated body to deflect; and detecting the position of the distal end of the elongated body by visualizing a location of the pull ring that is at least in part composed of the radiopaque material via fluoroscopy imaging.

Another broad aspect is a marker band for use in a steerable catheter or introducer sheath to perform medical procedures, wherein the marker band comprises an inner material composed at least in part of tantalum and is gold plated.

In some embodiments, the marker band may include apertures interspersed on an outer surface of the marker band.

In some embodiments, the apertures may go through the marker band, spanning the thickness of the marker band.

In some embodiments, each of the apertures may have a circular, oblong or elliptical cross-sectional shape.

In some embodiments, at least one of the apertures may have a three-lobe cross-sectional shape.

In some embodiments, the marker band may be fused to one or more pull wires to form a pull wire assembly.

In some embodiments, the marker band may be ring-shaped.

Another broad aspect is an introducer sheath used in medical procedures including the marker band as defined herein integrated into an end of the introducer sheath for visualizing the end of the introducer sheath during a medical procedure.

In some embodiments, the marker band may be fused to one or more pull wires to form a pull wire assembly, and wherein the marker band further acts as a pull ring of a steering system for the introducer sheath.

Another broad aspect is a steerable catheter device for use in medical procedures. The catheter device includes an elongated body with a proximal end and a distal end, the elongated body comprising an inner lumen; a marker band as defined herein integrated into the distal end of the elongated body for identifying a position of the distal end during a medical procedure; and a steering system for deflecting the elongated body.

In some embodiments, the steering system may include one or more pull wires, and wherein each of the one or more pull wires may be fused to the marker band at a distal end of the each of the one or more pull wires, the marker band acting as a pull ring of the steering system.

In some embodiments, the catheter device may include a handle at the proximal end of the elongated body, the handle comprising a steering control mechanism, the one or more pull wires fused at a proximal end of the one or more pull wires to the steering control mechanism, and wherein tension applied to the one or more pull wires by the steering control mechanism causes the elongated body to deflect.

In some embodiments, the steering system may include a pull ring and one or more pull wires fused to the pull ring, the pull ring integrated into the elongated body at the distal end of the elongated body at a location next to the marker band.

Another broad aspect is a use of the introducer sheath as defined herein or the catheter device as defined herein for visualizing the tip of the introducer sheath or of the catheter device during a medical procedure.

In some embodiments, the medical procedure may include a cardiac procedure.

Another broad aspect is a pull ring adapted for connecting to one or more pull wires, wherein the pull ring and the one or more pull wires provide a pull wire assembly for use in a catheter or sheath. The pull ring includes a proximal end and a distal end defining a width of the pull ring; an outer surface and an inner surface defining a thickness of the pull ring; and apertures distributed about the outer surface, wherein a depth of each of the apertures is at most the thickness of the pull ring, wherein each of the apertures is located closer to the proximal end than the distal end, and whereby the one or more pull wires are each joinable to the pull ring at a location closer to the proximal end than the distal end of the pull ring.

In some embodiments, the pull ring may include diving boards at the proximal end of the pull ring, wherein each of the one or more diving boards may be configured to receive one of the one or more pull wires.

In some embodiments, each of the apertures may have a circular, oblong or elliptical cross-sectional shape.

In some embodiments, at least one of the apertures may have a three-lobe cross-sectional shape.

In some embodiments, the apertures may span the thickness of the marker band.

In some embodiments, the apertures may be further distributed radially at nonuniform intervals with respect to one-another.

In some embodiments, the marker band may be ring-shaped.

Another broad aspect is a pull wire assembly including the pull ring as defined herein, further comprising the one or more pull wires, wherein for each of the one or more pull wires there is one or more of the apertures located in proximity to the each of the one or more pull wires.

Another broad aspect is an introducer sheath for use in medical procedures comprising the pull wire assembly as defined herein, wherein the pull wire assembly is integrated into the introducer sheath and the pull ring is anchored at an end of the introducer sheath.

Another broad aspect is a steerable catheter device for use in medical procedures including an elongated body with a proximal end and a distal end, the elongated body comprising an inner lumen; and the pull wire assembly as defined herein, wherein the pull ring is integrated into the elongated body at the distal end of the elongated body, wherein the one or more pull wires run along the elongated body from the distal end of the elongated body to the proximal end of the elongated body, and wherein a position of the distal end of the elongated body may be viewed during a medical procedure by visualizing the position of the pull ring.

In some embodiments, the catheter device may include a handle located at the proximal end of the elongated body.

In some embodiments, the handle may include a steering control mechanism, and wherein tension applied to the one or more pull wires by the steering control mechanism may cause the elongated body to deflect.

Another broad aspect is a use of the introducer sheath as defined herein or the catheter device as defined herein for visualizing the tip of the introducer sheath or of the catheter device during a medical procedure.

In some embodiments, the medical procedure may include a cardiac procedure.

BRIEF DESCRIPTION OF THE DRAWINGS

The invention will be better understood by way of the following detailed description of embodiments of the invention with reference to the appended drawings, in which.

DETAILED DESCRIPTION

Definitions

In the present disclosure, by "radiopaque" it is meant opaque to X-rays or similar radiation, where the level of radiopacity may be determined, e.g., per the standard tests for determining radiopacity ASTM F640-12, DIN 13273, such that the obstruction or limiting the passage of radian energy by the material is sufficient for visualization during a medical procedure when performing a visualization technique (e.g. fluoroscopy). The more radiopaque a component or assembly is, the lighter or whiter it will appear on film or display during a visualization technique.

Moreover, "radiopacity" is the ability of a component or assembly made of various materials (metal, alloy, ceramic, composite, polymer or combination thereof) to obstruct or limit the passage of radian energy such as x-ray or fluoroscopy. Different components or assembly will have different levels of radio-opacity. The more radiopaque a component or assembly is lighter or whiter it will appear on film or display. Generally, the higher the molecular weight and the denser a component or assembly is, the more radio-opaque it is. For example, interventional cardiologists wear lead aprons to protect themselves from harmful overexposure to x-ray and fluoroscope. Lead has a high molecular weight and is a dense material.

In the present disclosure, by "medical procedure", it is meant a surgical intervention or minimally invasive procedure performed on a patient. Medical procedures include cardiac procedures, pulmonary procedures, urological procedures, etc. Cardiac procedures include, but are not limited to, cryoablation, radio frequency ablation, laser ablation, and/or microwave ablation, cardiac mapping, transceptal procedures, transcatheter aortic valve replacement, etc.

Steerable Catheter or Introducer Sheath:

The present disclosure relates to steerable sheaths and introducer catheters used for medical procedures.

Figure 1:
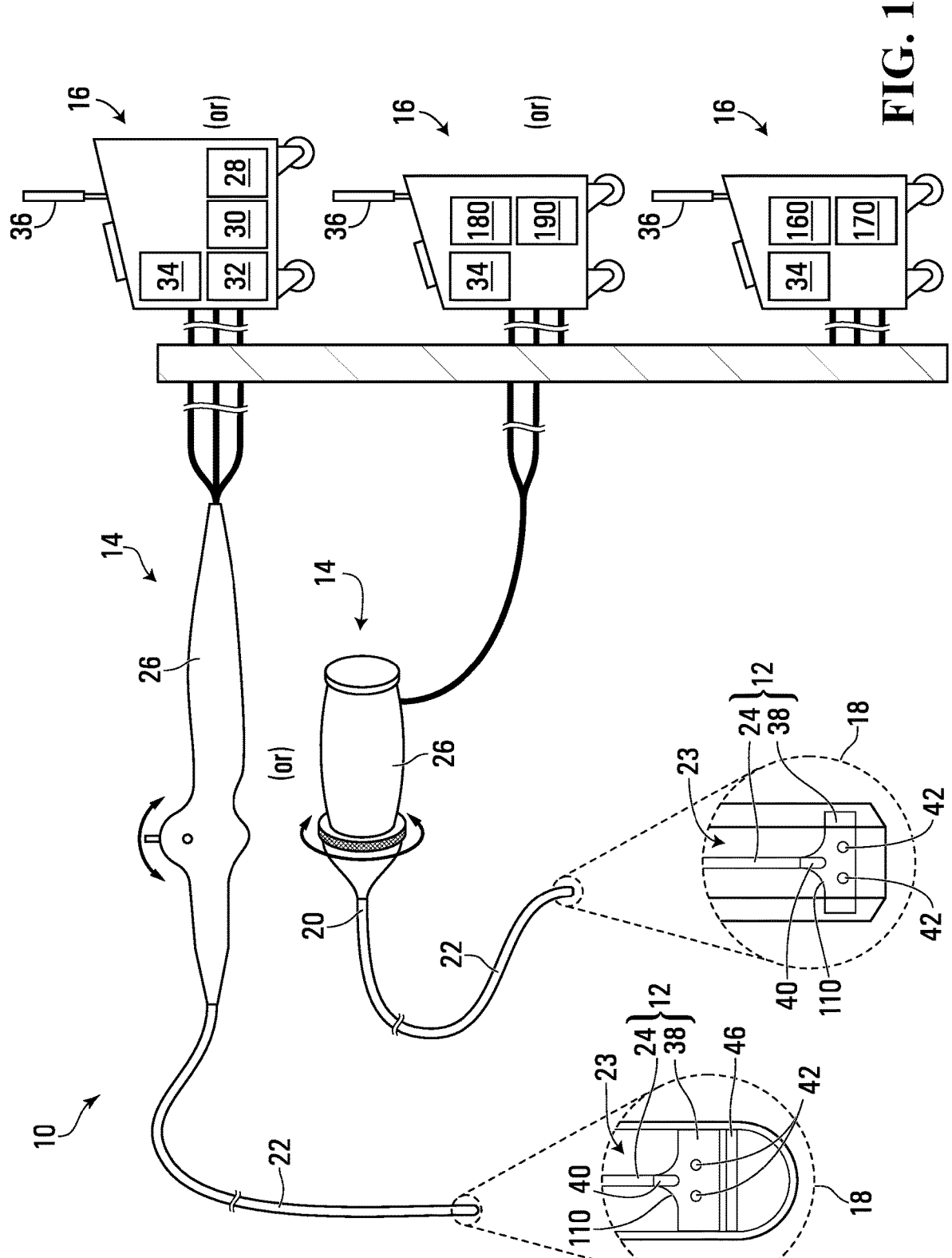
FIG. 1 is a drawing of an exemplary system including an exemplary pull wire assembly.

Referring now to FIG. 1, a system 10 including a pull wire assembly 12 is shown. The pull wire assembly 12, acting as a steering deflection mechanism, may generally include a pull ring 38 and one or more pull wires 24. The system 10 may generally include a medical device 14 (e.g. a steerable catheter such as a trans-catheter valve replacement device, a diagnostic catheter or an ablation catheter, etc.) The medical device 14 may include a distal end 18, a proximal end 20 and a flexible elongate shaft 22 having one or more lumens therein 23. The distal end 18 of the flexible elongate shaft 22 may be capable of in-plane and/or out-of-plane deflection and is steerable by one or more pull wires 24. The proximal end 20 of the medical device 14 may be affixed to a handle 26 having various inlets, outlets, steering control mechanisms (for example, knobs, toggles, etc.) Further, the one or more pull wires 24 may be either coupled to or routed through the handle 26. The medical device 14 may be in fluid and/or electrical communication with a console 16 that may include an energy generator 28 (for example, a radio frequency generator), a refrigerant reservoir 30, a power source 32, a computer 34, a display 36, and/or various user control devices (for example, buttons, knobs, valves, keyboard, touch screen, foot pedals, etc.) The medical device 14 may be adapted for diagnostic or treatment using any energy modality (for example, cryoablation, radio frequency ablation, laser ablation, and/or microwave ablation) and/or medical procedure or diagnostics that is facilitated by using a steerable catheter (for example, cardiac mapping or valve repair or replacement). FIG. 1 illustrates different kinds of consoles 16. For instance, the console 16 may be a cryo console with a refrigerant reservoir 30, a power source 32, a computer 34, a display 36, etc. In other embodiments, the console 16 may be a RF (radio frequency) console with a computer 34, an RF generator 180, an irrigation cooling unit 190, a power source, etc. The console 16 may be a laser console with a computer 34, a laser source 160, a laser chiller 170, a power source, etc.

The pull ring 38 of the pull wire assembly 12 is affixed to the inside of the distal end 18 of the medical device's 14 flexible elongated shaft 22 and the one or more pull wires 24 are coupled to the pull ring 38. When a user manipulates the pull wires 24, the distal end 18 of the medical device 14 is deflected (i.e. steered) in the direction of the force being exerted on the pull ring 38 by the one or more pull wires 24. As is shown in greater detail in FIGS. 3B, 4, the pull ring 38 may generally include one or more receiving slots 40, each of which receiving a pull wire 24, and a plurality of apertures 42.

Figure 2:
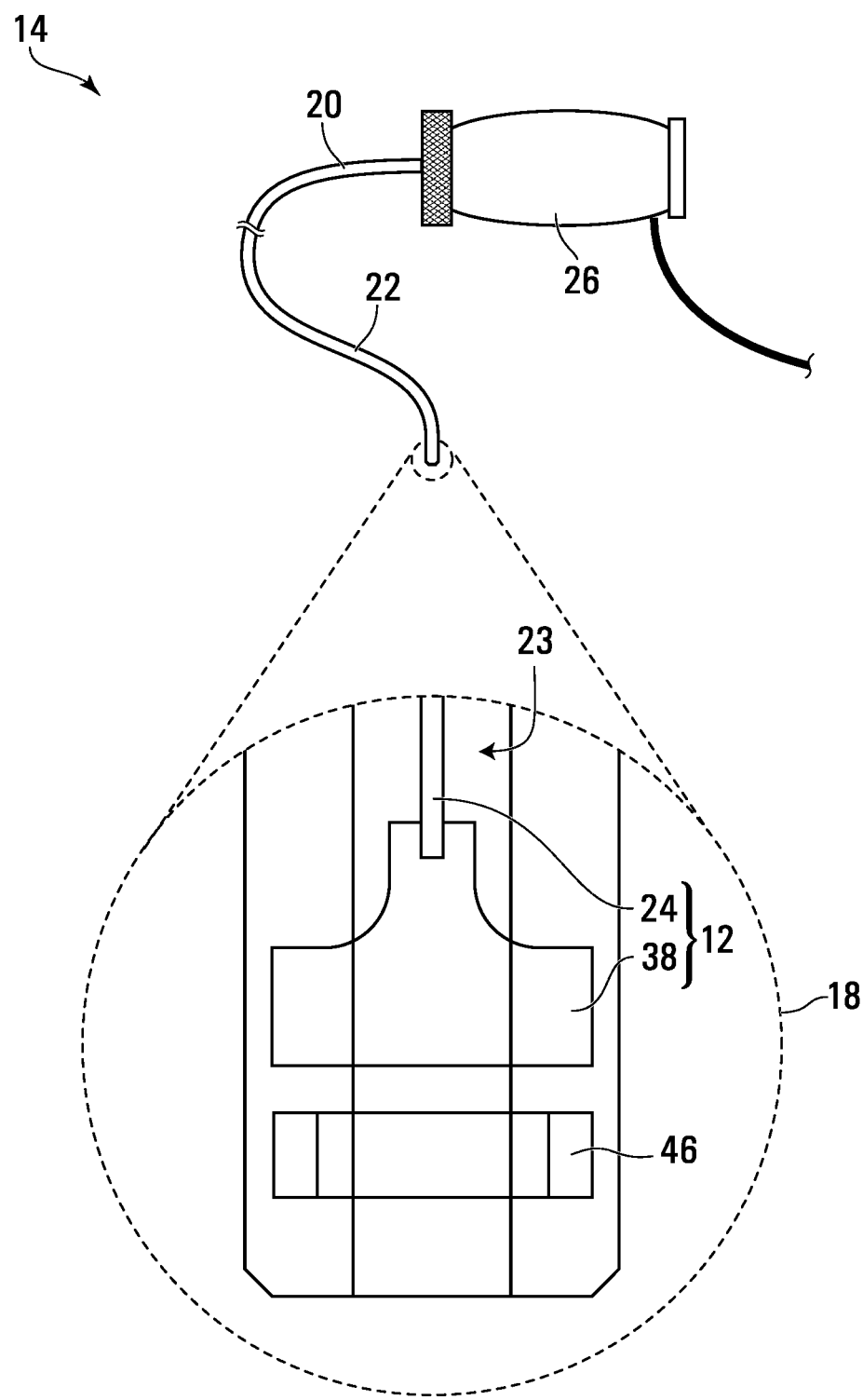
FIG. 2 is a drawing of an exemplary introducer sheath with an exemplary pull wire assembly.

As shown in FIG. 2, the medical device 14 may also be an introducer sheath.

Figure 3A:
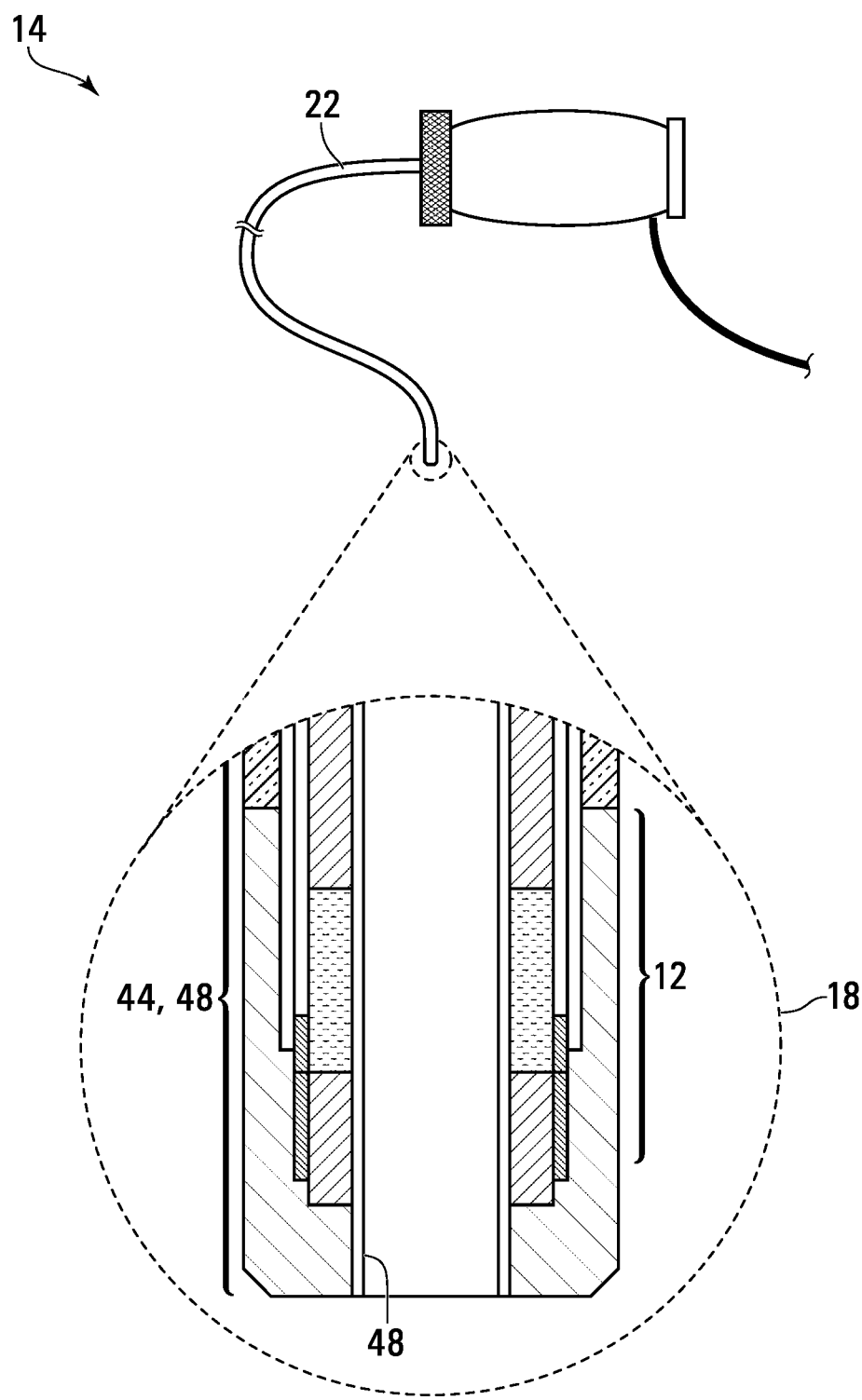
FIG. 3A is a drawing of an exemplary introducer sheath with a blown-up view of the distal end of its flexible elongated shaft.

Referring now to FIG. 3A, a cross-sectional view of a medical device 14 (for example, a catheter) shaft 22 is shown. The cross section shows a typical distribution of thermoplastic 44/48 between the inner lining 48 of the catheter shaft 22 and the pull wire assembly 12. As shown and described in FIG. 3A, melted thermoplastic 44/48 of the catheter shaft inner lining 48 and the inner ring layer 44 of the pull wire assembly 12 melds or blends as the melting temperature of the thermoplastic 44/48 is reached. As the shaft 22 is allowed to cool, the thermoplastic 44/48 hardens and thereby strengthens the point of connection between the distal end 18 of the catheter shaft 22 and the pull wire assembly 12. Although not shown in FIG. 3A, the catheter shaft 22 may include additional layers or elements.

Figure 3B:
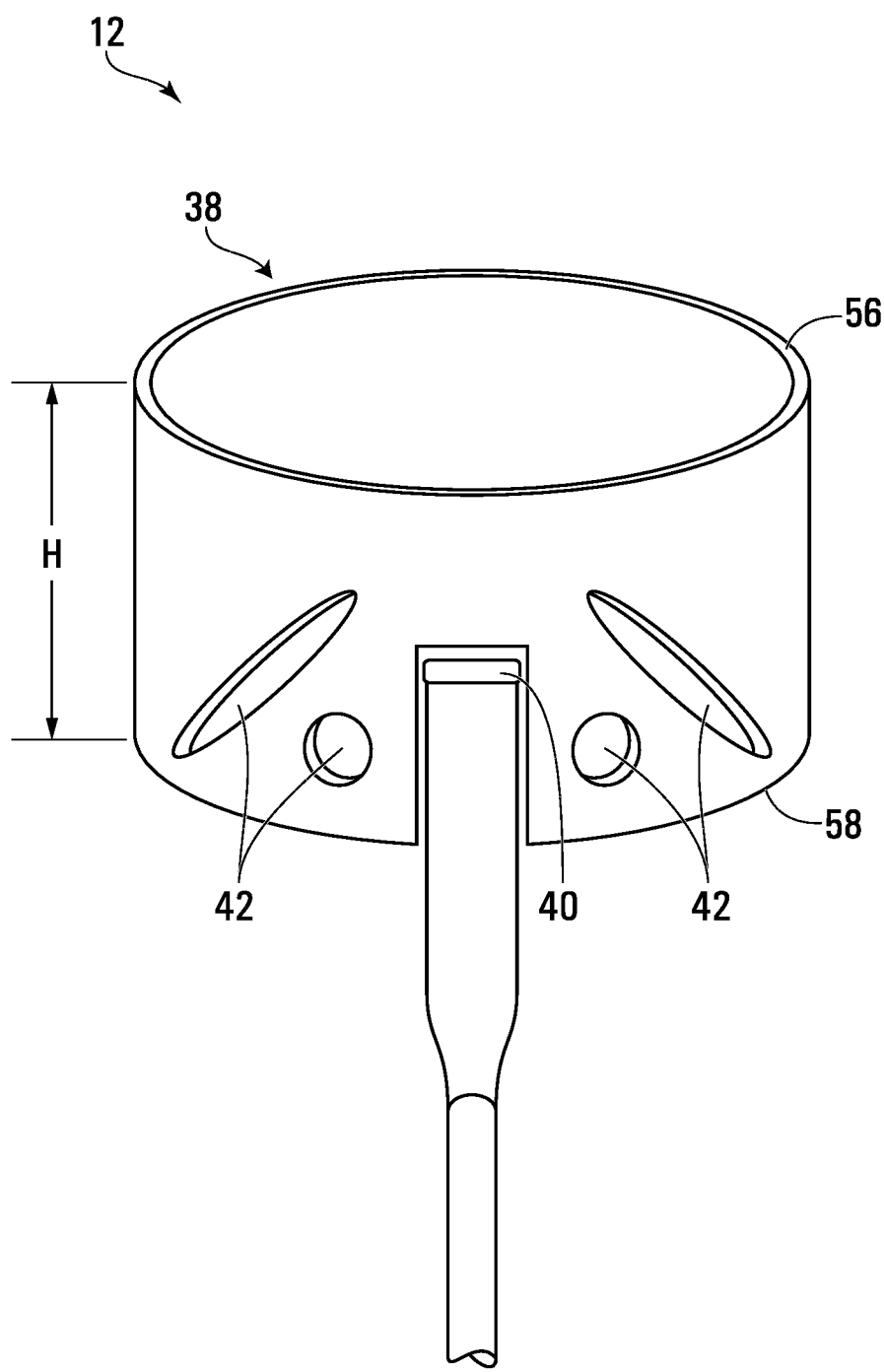
FIG. 3B is a drawing of an exemplary pull wire assembly.

Exemplary Pull Wire Assembly:

Referring now to FIG. 3B, a pull wire assembly 12 is shown. The pull wire assembly 12 (or anchor mechanism) as shown in FIG. 3B generally includes a pull ring 38 and one or more pull wires 24 having a circular or round cross section (also referred to as a "round pull wire"). The pull wire assembly 12 is located in the distal end 18 of a catheter flexible elongated shaft 22, and the shaft 22 may include a lining 48 composed of the same thermoplastic as the inner ring layer 44. Thermoplastic in general, such as when the inner ring layer 44 and shaft lining 48 melt together, also referred to a reflowing, is referred to as "thermoplastic 44/48." The thermoplastic inner ring layer 44 is in contact with the inner surface 50 of the pull wire ring 38 and may be approximately 0.05 mm to approximately 0.5 mm thick. Further, the thermoplastic inner ring layer 44 may have a height HTL that is greater than the height H of the pull wire ring 38.

The pull wire assembly 12 may be coupled to the catheter shaft 22 by heating the shaft 22 to a melting temperature of the thermoplastic 44/48 used in the pull wire assembly 12 and the shaft inner lining 48. Specifically, as the thermoplastic 44/48 is heated and melts, the thermoplastic inner ring layer 44 of the pull wire assembly 12 will meld or blend with the thermoplastic inner lining 48 of the catheter shaft 22, thereby affixing the pull wire assembly 12 to the distal end 18 of the medical device 14. Further, when the pull ring 38 has apertures 42, melted thermoplastic 44/48 may also flow through the apertures 42 in the pull wire ring 38 to give added strength to the pull wire assembly 12 and shaft 22 point of connection when the thermoplastic 44/48 hardens.

Figure 8:
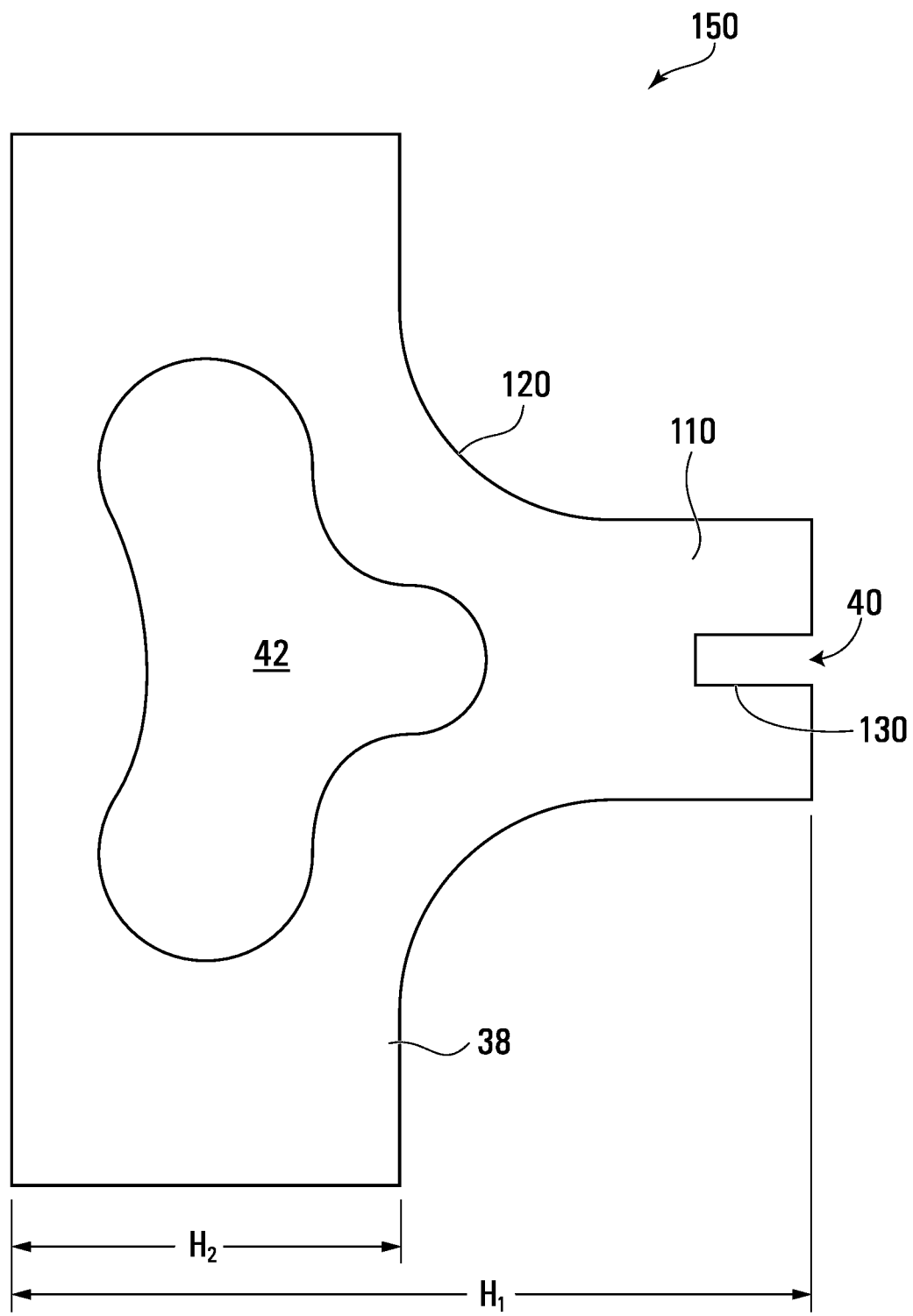
FIG. 8 is a drawing of a top-down view of an exemplary pull ring with an exemplary diving board, an exemplary aperture and an exemplary notch.

As shown in FIG. 3B, the apertures 42 may be of a different shape one with respect to one another. Moreover, the apertures 42 may have a circular cross-section, an elliptical cross-section, or may have a three-lobe cross section as illustrated in FIG. 8. It will be understood that the cross-sectional shape of the apertures 42 may vary without departing from the present teachings.

The apertures 42 may have a depth that is equal to the thickness of the pull ring 38, spanning through the pull ring 38.

Moreover, at least some of the apertures 42 are located closer to one end of the pull ring 38 than to the other end of the pull ring 38. For instance, as shown in the example of FIG. 3B, the apertures 42 are closer to the first side 58 of the pull ring 38, the side where the pull wire 24 extends from, than the second side 56. The apertures 42 may also be positioned in proximity to the point where the pull wire 24 is fused to the pull ring 38.

Figure 4:
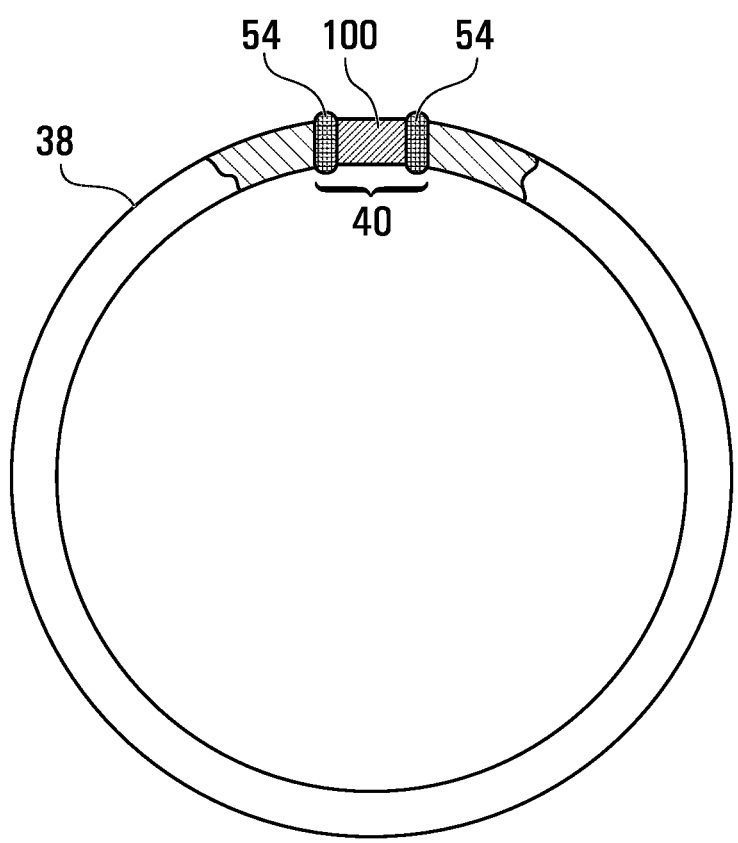
FIG. 4 is a drawing of a front, cross-sectional view of an exemplary pull wire assembly.

Continuing to refer to FIG. 4, the pull wire ring 38 may include a single receiving slot 40 if only one pull wire 24 is used for steering the distal end 18 of the medical device 14. In general, the receiving slot 40 may be substantially straight for receiving a straight rounded pull wire 24, lobe-shaped for receiving a knobbed round pull wire 24, or may continue from the first edge to the second edge of the pull ring 38, thereby breaking the continuity of the entire pull ring 38 (not shown). The straight receiving slot 40 of FIG. 5 continues from the first side 58 of the pull ring 38 to a distance from the second side 56, thereby preserving the continuity of only the second side 56 and portion of the pull ring 38 proximate thereto. As a non-limiting example, the width of the receiving slot 40 may be approximately 0.30 mm, and the height may be approximately 1.14 mm. The distance between the receiving slot 40 and the second side 56 of the pull ring 38 may be, for example, between approximately 15% and approximately 55% of the height of the pull ring 38. However, the receiving slot 40 and pull ring 38 may have any measurements that are appropriate for the pull wire 24 and medical device 14 assembly used.

Figure 5:
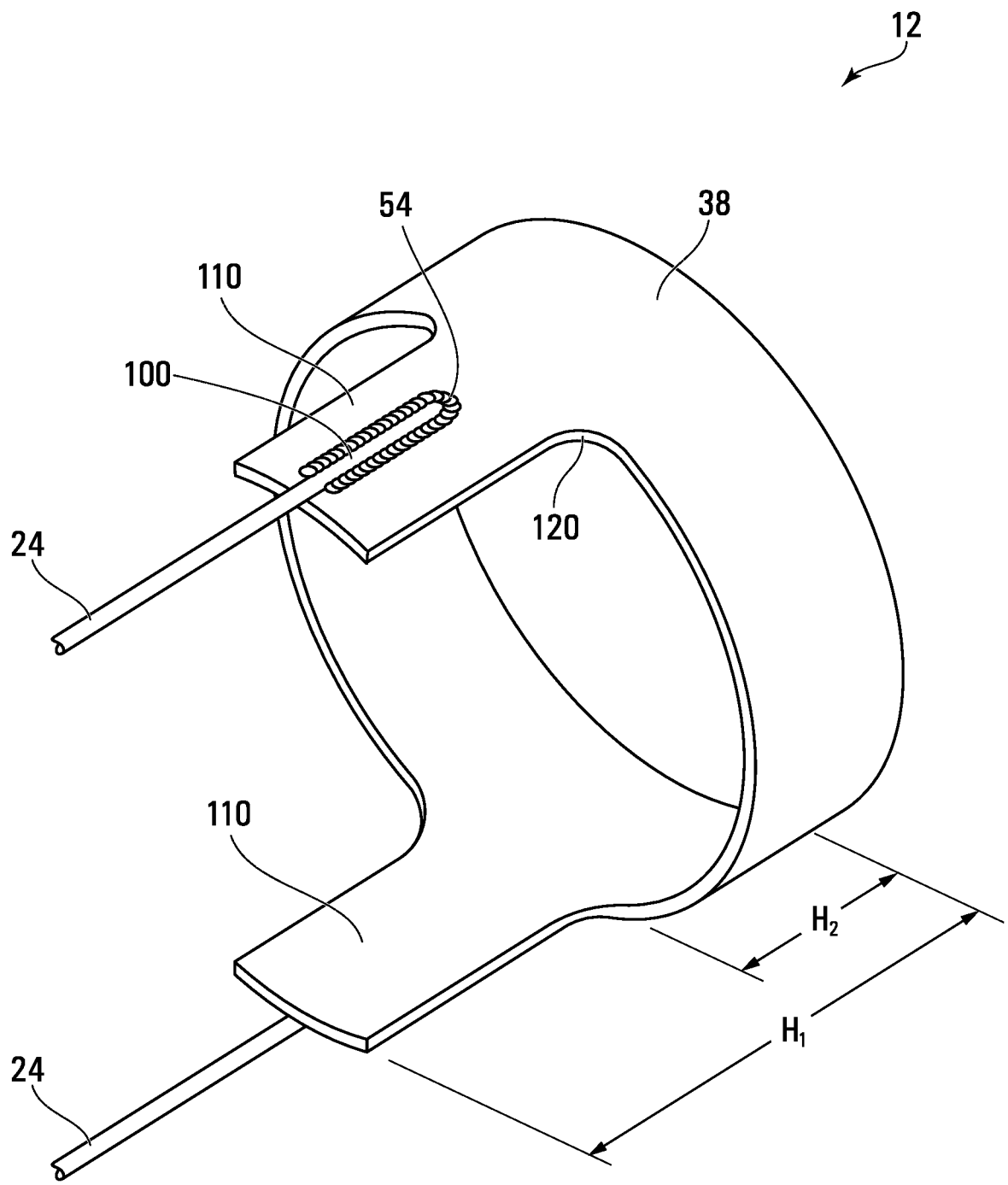
FIG. 5 is a drawing of a perspective view of an exemplary pull wire assembly with exemplary diving boards, where each diving board receives a pull wire.

Reference is now made to FIG. 5, illustrating an exemplary pull wire assembly 12 where the pull ring 38 includes diving boards 110. Each of the diving boards 110 is configured to receive a pull wire 24. The pull wire 24 may be directly fused to the diving board 110 at a fusion point 100. In other examples, the diving board 110 may include a slot (e.g. notch) 40 for receiving the end of the pull wire 24, where the end of pull wire 24 may be, for instance, flattened for increasing the contact area when fused to the diving board 110.

The diving board 110 projects from the body of the pull ring 38. The diving board 110 may be made from the same material as the pull ring 38.

When more than one diving board 110 is present, each of the diving boards may be radially symmetric with respect to one another.

The plane of the diving board 110 projecting from the body of the pull ring 38 may be slightly curved, following the curvature of the body of the pull ring 38.

In some embodiments, the edges 120 of the diving board 110 that merge with and define the first side 58 of the pull ring 38 may be arcuate, for deflecting force that is exerted by the pull wire 24 on the diving board 110.

Therefore, the diving board(s) 110 and/or the aperture(s) 24 may reduce stress exerted on both the pull ring 38 and the pull wire 24, reducing the risk of failure of either component of the pull wire assembly 12 under the force exerted by the pull wires 24.

The pull wire 24 is fused to the pull ring 38, and in some embodiments, the diving board 110. Fusing the pull wire 24 to the pull ring 38 creates an amalgam of the material of the pull wire 24 and the material of the pull ring 38 at the fused pool 54. This amalgam is important to create a bond between the pull wire 24 and the pull ring 38 that is capable of resisting the tension applied by the pull wire 24. The resulting amalgam is also necessary for joining the pull wire 24 and the pull ring 38 when the pull wire 24 is made from a different material from the pull ring 38. The pull ring 38 may be made from a radiopaque material such as tantalum, molybdenum or a combination thereof. The pull wire may be made from any suitable material, such as stainless steel, titanium, Nitinol, or an alloy thereof. In some embodiments, the amalgam is homogenous.

Tantalum is a dense material (therefore good at absorbing x-rays) and is also very strong and hard (e.g. less flexible than steel). Therefore, when the pull ring 38 is composed at least in part from tantalum, having a diving board 110 that is more flexible than the rest of the pull ring 38 results in the diving board 110 flexing under the force exerted by the pull wire 24. As such, this flexing of the diving board 110 may reduce the bending of the pull wire 24 and may increase the durability of the pull wire 24.

In order to arrive at the fused pool 54, the material of the pull wire 24 and the material of the pull ring 38 are heated to their respective melting temperatures where the two created melting pools that are at very different temperatures are amalgamated (in some examples, homogeneously amalgamated) together and controlled dynamically throughout the process. In some embodiments, the fused pool 54 may be achieved using two laser heads, where each laser head is used for a specific material. Each of the laser heads may also have integrated optical coherence tomography for dynamically monitoring the melting pool of the material, where laser properties (e.g. laser power, pulse rate, pulse duration, focal point, feed fate, etc.) may be adjusted as a function of feedback received via the optical coherence tomography. The dynamic monitoring may be helpful when materials with dissimilar properties are used, such as materials having different optical properties and melting temperatures. In some embodiments, the heat affected zone resulting from the laser may be equal or less than 50 microns, with a weld zone maintained to a micro size volume, and where the part size may be in sub-millimeters. It will be understood that other methods of achieving the fused pool 54 (and dynamically monitoring the welding process) may be used with departing from the present teachings.

The width from the end of the diving board 110 to the opposite end of the pull ring 38 may be H1 as shown in FIG. 5. The width of the portion of the pull ring 38 that precedes the diving board 110 may be H2.

Figure 6:
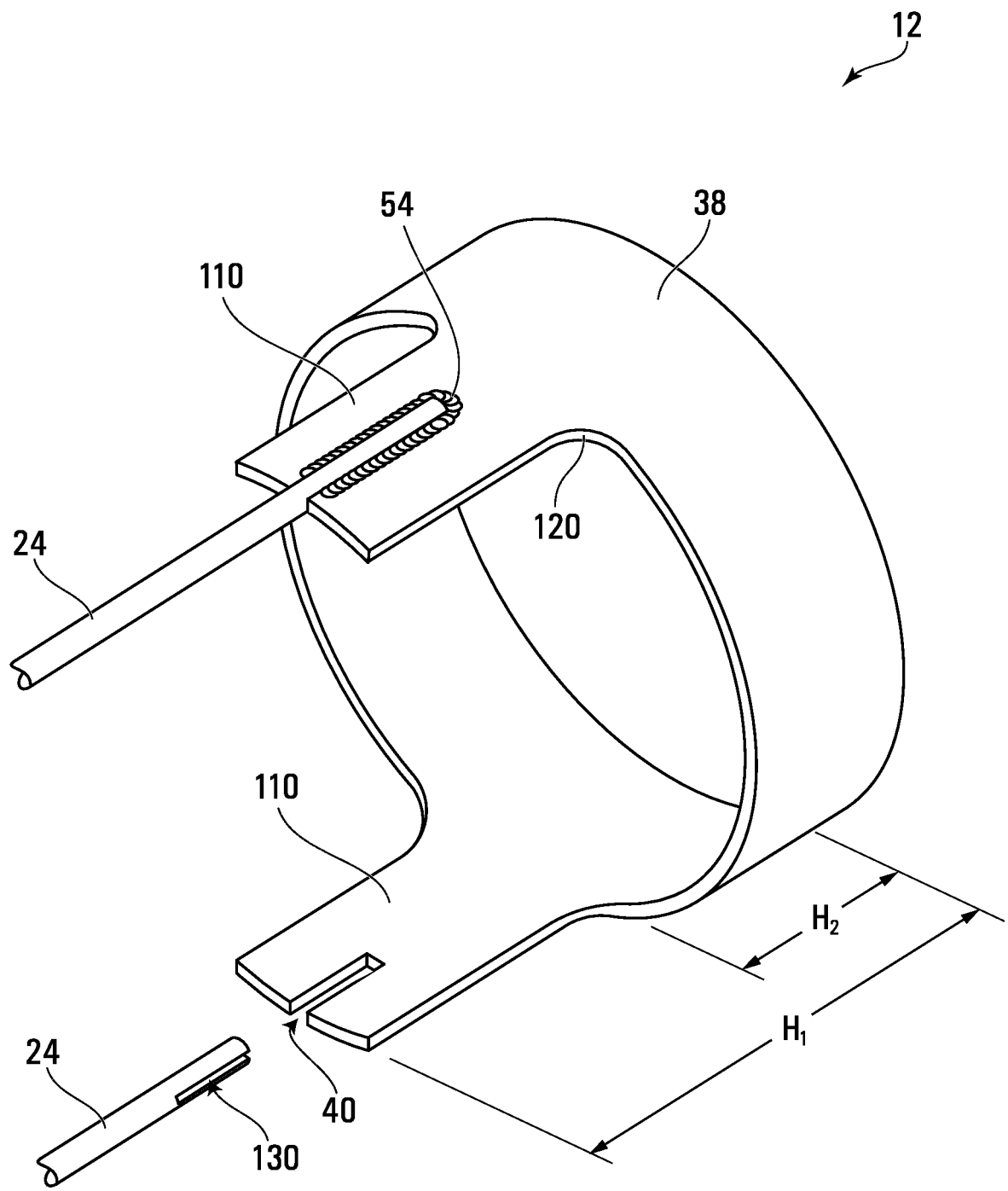
FIG. 6 is a drawing of a perspective view of an exemplary pull wire assembly with exemplary diving boards, where each diving board receives a pull wire in a notch.

As shown in FIG. 6, in some embodiments, the end of the pull wire 24 may have a protrusion 130 at its end obtained by electrical discharge machining (EDM). The protrusion of the wire 24 may be adapted to be fitted into a corresponding slot 40 of the pull ring 38 (including at its diving board 110).

In some examples, the depth of the slot 40 may be less than the thickness of the pull ring 38, where the slot 40 does not span through the pull ring 38. In other examples, the slot 40 spans through the pull ring 38, and as such, the slot 40 has a depth that is equal to the thickness of the pull ring 38.

Figure 7:
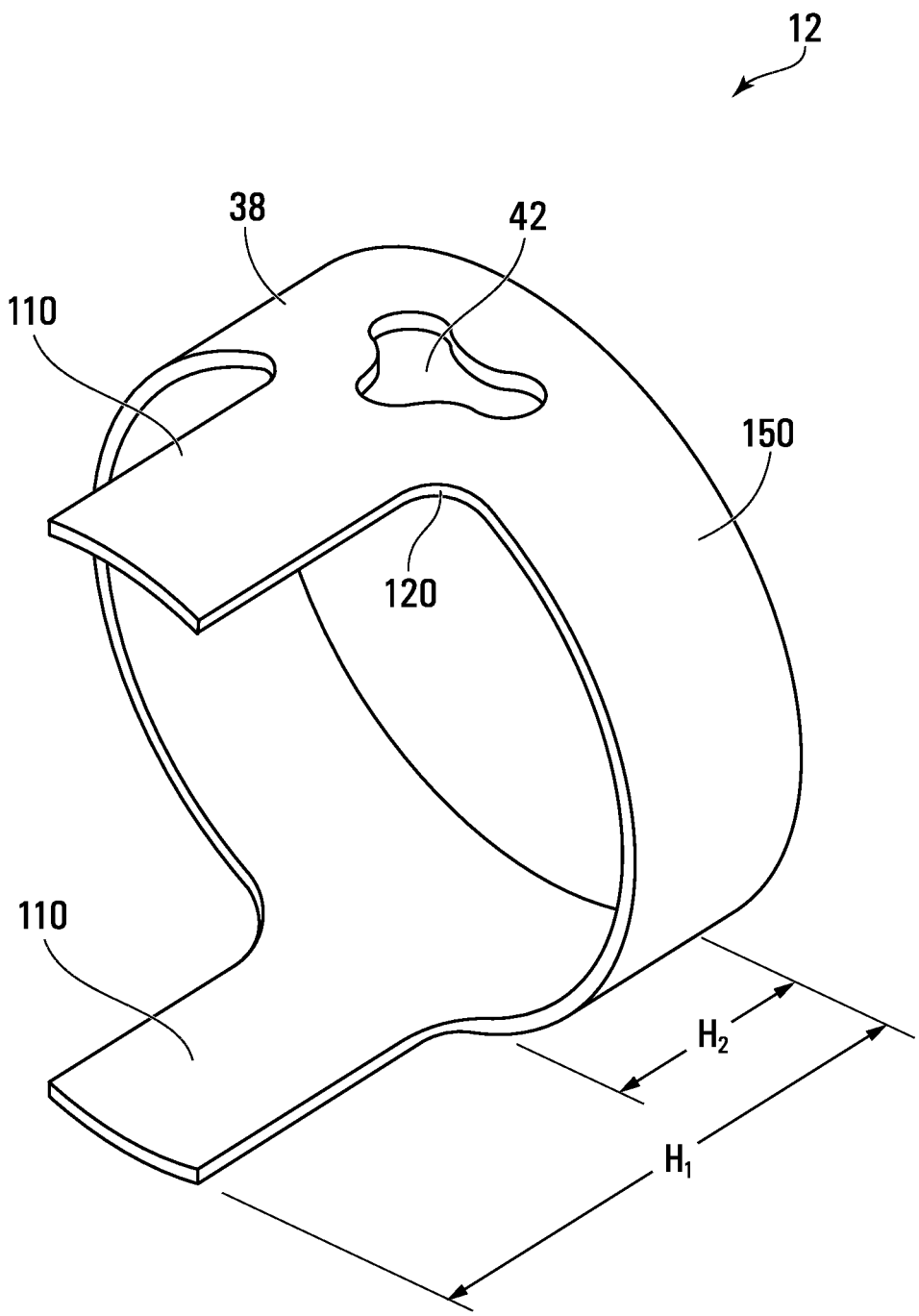
FIG. 7 is a drawing of a perspective view of an exemplary pull ring with exemplary diving boards and one exemplary aperture.
Figure 9A:
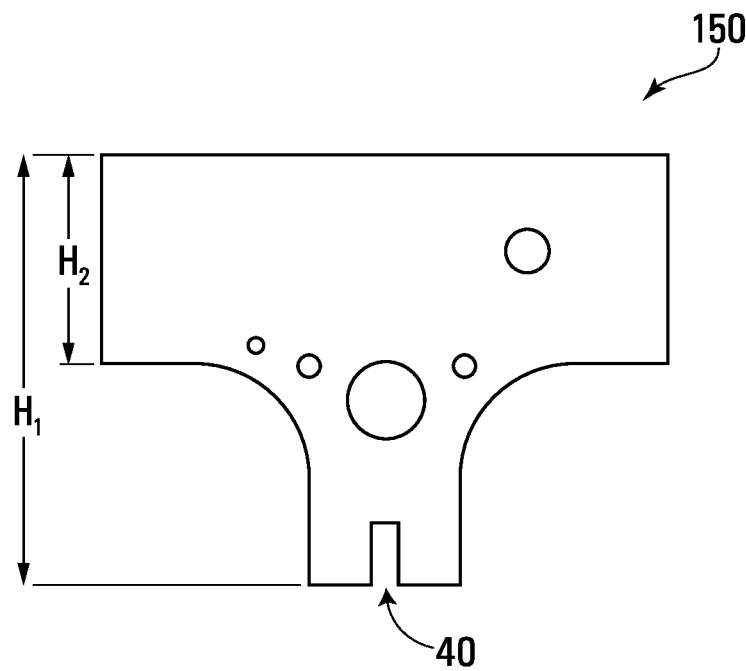
FIG. 9A is a drawing of a top-down view of exemplary pull rings, wherein each pull ring has an exemplary diving board, an exemplary aperture and an exemplary notch.
Figure 9A:
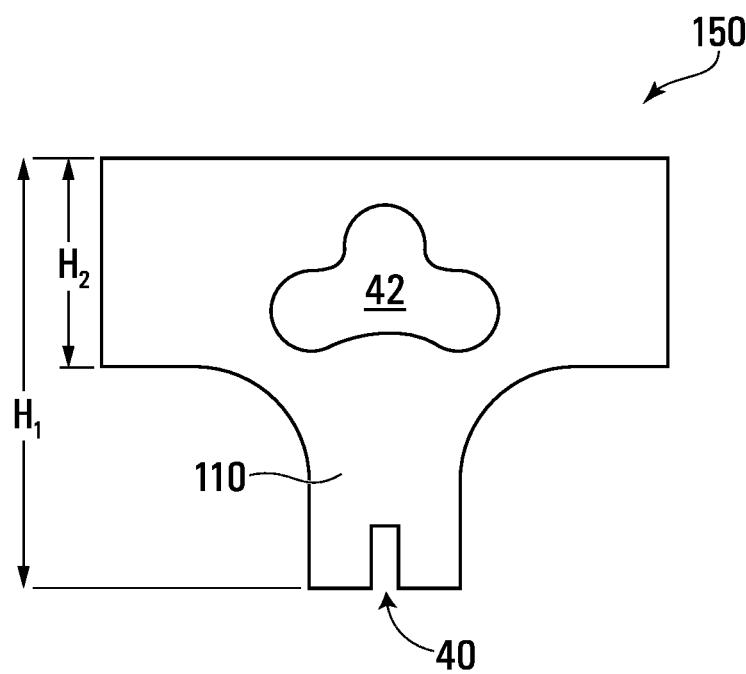

In some examples, as shown in FIGS. 7, 8 and 9A, the pull ring 38 includes a single reflow aperture 42. This aperture 42 may have a three-lob shape (e.g. as illustrated in FIG. 7). The aperture 42 may be aligned with the point at which the pull wire 24 joins the pull ring 38 along the width of the pull ring 38.

In other examples, there may be more than one three-lobe aperture.

Figure 9B:
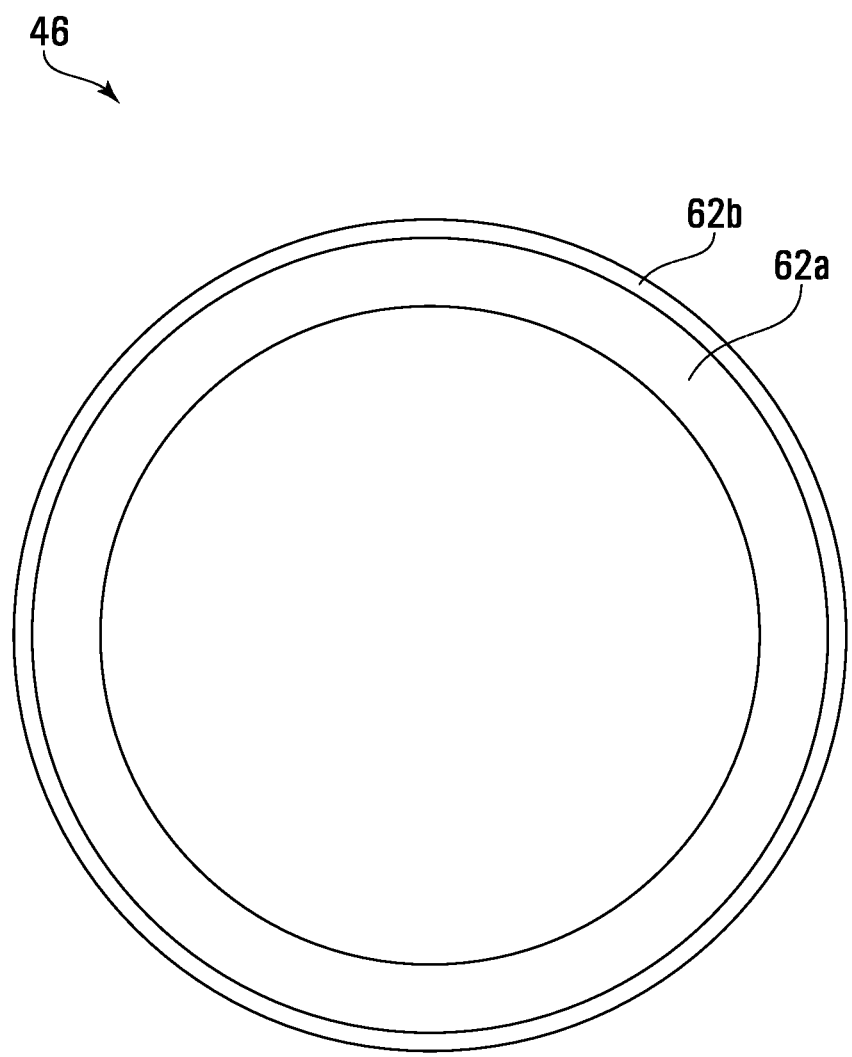
FIG. 9B is a drawing of a front cross-sectional view of an exemplary marker band with gold plating.

Exemplary Marker Band:

Reference is now made to FIG. 9B, illustrating an exemplary marker band 46 for use in a steerable catheter or introducer sheath comprising an inner layer 62a made from a radiopaque material such as tantalum, molybdenum, or an alloy thereof, and an outer radiopaque layer 62b made from a material that is different from that of the inner layer 62a. The outer layer 62b may be made from gold (e.g. where the marker band 46 may be gold-plated). The exemplary marker band 46 may provide for enhanced visualization when performing such visualization techniques as fluoroscopy.

In some embodiments, the marker band may be ring shaped. In other embodiments, the marker band can be a disk located at the tip of the distal end of the shaft 22. In will be appreciated that the marker band may have any shape adapted to allow visualization of an end or portion of the shaft of the steerable catheter or introducer sheath during a medical procedure using a visualization technique.

In some embodiments, the marker band 46 may also be employed as a pull ring as described herein, wherein the pull wires 24 are fused to the marker band 46 as described herein, anchoring the ends of the pull wires 24 to the distal end of the shaft 22.

In other examples, the steerable catheter or introducer sheath including the gold-plated marker band 46 may include a distinct pull ring, the one or more pull wires joined to the pull ring.

Exemplary Method of Steering the Catheter Device:

The present disclosure also relates to steering a catheter device during a medical procedure, the catheter device inserted into a patient, where the tip of the catheter device can be visualized using, for instance, fluoroscopy. For illustrative purposes, reference will be made to the catheter device 14 and the pull ring assembly 12. However, it will be understood that any other catheter device and/or pull ring assembly in accordance with the present teachings may be used.

In order to navigate the catheter device 14 during the medical procedure, the distal end of the shaft 22 is caused to deviate. Deviation results from tension being applied to the distal end of the shaft 22, the tension applied by the pull wire 24 fused to the pull ring 38, the pull wire 24 tugging on the pull ring 38 that is anchored to the distal end of the shaft 22. The pull wires 24 may be controlled by the medical practitioner at the level of the handle 26, where the handle 26 may include a steering control mechanism.

The distal end of the shaft 22 of the catheter device 14 is then detected by visualizing the position of the pull ring 38, the pull ring 38 being composed of a radiopaque material. As such, the pull ring 38 acts both as a marker band, identifying the distal end of the shaft 22, and as an anchor for causing the deflection of the distal end of the shaft 22 of the catheter device 14.

Due to the dual function performed by the pull ring 38, the catheter device 14 does not require a marker band separate from the pull ring 38. This reduction of components at the distal end of the shaft 22 reduces the rigidity of the distal end of the shaft 22 (e.g. as the thermoplastic material used to affix a marker band and/or a pull ring may be more rigid than that of the rest of the shaft 22). The pull ring 38 is also placed nearer the end of the distal end of the shaft 22 then if a marker band were equally present. As such, having a pull ring 38 that also acts as a marker band allows for a more accurate deflection of the tip of the shaft 22 (the pull ring 38 placed nearer the distal end of the shaft 22 than if the marker band were present, where the pull ring 38 may provide anchoring of the shaft 22 at a point nearer the tip of the shaft 22), improving navigation of the catheter device 14 in the patient during the medical procedure.

Although the invention has been described with reference to preferred embodiments, it is to be understood that modifications may be resorted to as will be apparent to those skilled in the art. Such modifications and variations are to be considered within the purview and scope of the present invention.

Representative, non-limiting examples of the present invention were described above in detail with reference to the attached drawing. This detailed description is merely intended to teach a person of skill in the art further details for practicing preferred aspects of the present teachings and is not intended to limit the scope of the invention. Furthermore, each of the additional features and teachings disclosed above and below may be utilized separately or in conjunction with other features and teachings.

Moreover, combinations of features and steps disclosed in the above detailed description, as well as in the experimental examples, may not be necessary to practice the invention in the broadest sense, and are instead taught merely to particularly describe representative examples of the invention. Furthermore, various features of the above-described representative examples, as well as the various independent and dependent claims below, may be combined in ways that are not specifically and explicitly enumerated in order to provide additional useful embodiments of the present teachings.

What is claimed is:

1. A pull wire assembly for integrating into and anchoring an end of a steerable catheter or introducer sheath used in medical procedures, comprising:

a pull ring made at least in part from a radiopaque material that, when integrated into the end of the steerable catheter or the introducer sheath, allows for visualizing the end of the steerable catheter or the introducer sheath during a medical procedure; and one or more pull wires with a different material composition from that of said pull ring, wherein said one or more pull wires are each fused with said radiopaque material of said pull ring, wherein said fusion results in an amalgam of said radiopaque material and said pull wire material composition by heating the radiopaque material and the pull wire material composition to respectively a melting temperature of the radiopaque material and a melting temperature of the pull wire material composition while monitoring a melting pool of the radiopaque material and a melting pool of the pull wire material composition to adjust a heating of the radiopaque material separately from a heating of the pull wire composition based on the monitoring.

2. The pull wire assembly as defined in claim 1, wherein said pull ring is made from tantalum, molybdenum, a tantalum alloy, a molybdenum alloy or a combination thereof.

3. The pull wire assembly as defined in claim 2, wherein said pull ring is gold-plated.

4. The pull wire assembly as defined in claim 1, wherein said pull ring further comprises a diving board extending from said pull ring for each of said one or more pull wires, and wherein said each of said one or more pull wires is respectively fused to each diving board.

5. The pull wire assembly as defined in claim 4, wherein side portions of said each diving board are of an arcuate shape with a radius that blends into said pull ring for deflecting force exerted by said one or more pull wires onto said pull ring.

6. The pull wire assembly as defined in claim 1, wherein said pull ring further comprises apertures interspersed about said pull ring.

7. The pull wire assembly as defined in claim 6, wherein said pull ring comprises a proximal end and a distal end defining a width of said pull ring, and there is at least one of said apertures that is located closer to said proximal end of said pull ring than said distal end of said pull ring, and wherein said apertures are radially distributed at nonuniform intervals with respect to one-another.

8. An introducer sheath for use in medical procedures comprising the pull wire assembly as defined in claim 1, wherein said pull wire assembly is integrated into said introducer sheath and said pull ring is anchored at an end of said introducer sheath.

9. A steerable catheter device for use in medical procedures comprising:
- an elongated body with a proximal end and a distal end, said elongated body comprising an inner lumen; and
- the pull wire assembly as defined in claim 1, wherein said pull ring is integrated into said elongated body at said distal end of said elongated body, wherein said one or more pull wires runs along said elongated body from said distal end of said elongated body to said proximal end of said elongated body, and wherein a position of said distal end of said elongated body may be viewed during a medical procedure by visualizing the position of said pull ring.

10. The catheter device as defined in claim 9, further comprising a handle located at said proximal end of said elongated body.

11. A method of steering the catheter device as defined in claim 9 in a patient during a medical procedure comprising:
- applying tension to at least one of said one or more pull-wires fused to said pull ring, resulting in a force being applied to said pull ring that is integrated into said distal end of said elongated body, causing said elongated body to deflect; and
- detecting the position of said distal end of said elongated body by visualizing a location of said pull ring that is at least in part composed of said radiopaque material via fluoroscopy imaging.

\* \* \* \* \*